US012521501B2

(12) United States Patent
Buchberger

(10) Patent No.: US 12,521,501 B2
(45) Date of Patent: *Jan. 13, 2026

(54) AEROSOL DELIVERY DEVICE AND METHOD UTILIZING A FLAVORING RESERVOIR

(71) Applicant: Nicoventures Trading Limited, London (GB)

(72) Inventor: Helmut Buchberger, St. Florian (AT)

(73) Assignee: Nicoventures Trading Limited, London (GB)

( * ) Notice: Subject to any disclaimer, the term of this patent is extended or adjusted under 35 U.S.C. 154(b) by 321 days.

This patent is subject to a terminal disclaimer.

(21) Appl. No.: 18/296,544

(22) Filed: Apr. 6, 2023

(65) Prior Publication Data

US 2023/0241332 A1 Aug. 3, 2023

Related U.S. Application Data

(63) Continuation of application No. 18/175,933, filed on Feb. 28, 2023, which is a continuation of application (Continued)

(30) Foreign Application Priority Data

Aug. 13, 2014 (GB) ...................................... 1414331

(51) Int. Cl.

*A24F 47/00* (2020.01)
*A24F 40/30* (2020.01)
(Continued)

(52) U.S. Cl.

CPC ......... *A61M 15/0091* (2013.01); *A24F 40/30* (2020.01); *A24F 40/40* (2020.01); *A24F 40/485* (2020.01); *A61M 11/042* (2014.02); *A61M 15/06* (2013.01); *A24F 40/10* (2020.01); *A24F 40/20* (2020.01); *A61M 15/002* (2014.02); *A61M 15/0021* (2014.02); *A61M 2205/3653* (2013.01);
(Continued)

(58) Field of Classification Search

CPC ................................................ A61M 15/0091
See application file for complete search history.

(56) References Cited

U.S. PATENT DOCUMENTS 2,809,634 A 10/1957 Hirotada
3,356,094 A 12/1967 Drummond et al.
(Continued)

FOREIGN PATENT DOCUMENTS

CA 1301010 C 5/1992
CN 1248888 A 3/2000
(Continued)

OTHER PUBLICATIONS

"Application and File History for U.S. Appl. No. 16/842,153, filed Apr. 7, 2020".
(Continued)

*Primary Examiner* — Neil Abrams
(74) *Attorney, Agent, or Firm* — Merchant & Gould P.C.

(57) ABSTRACT

There can be provided a device configured to impart flavouring to an airstream admitted the device prior to the airstream reaching an aerosol generator of the device, the device thereby operable to deliver a flavoured aerosol from an outlet.

20 Claims, 8 Drawing Sheets

Related U.S. Application Data

No. 17/452,435, filed on Oct. 27, 2021, now Pat. No. 11,865,248, which is a continuation of application No. 17/443,170, filed on Jul. 21, 2021, now Pat. No. 12,186,479, which is a continuation of application No. 16/842,153, filed on Apr. 7, 2020, now Pat. No. 11,116,919, which is a continuation of application No. 16/377,331, filed on Apr. 8, 2019, now Pat. No. 10,674,771, which is a continuation of application No. 15/503,456, filed as application No. PCT/GB2015/052212 on Jul. 31, 2015, now Pat. No. 10,278,427.

(51) Int. Cl.

| | |
|---|---|
| ***A24F 40/40*** | (2020.01) |
| ***A24F 40/485*** | (2020.01) |
| ***A61M 11/04*** | (2006.01) |
| ***A61M 15/00*** | (2006.01) |
| ***A61M 15/06*** | (2006.01) |
| *A24F 40/10* | (2020.01) |
| *A24F 40/20* | (2020.01) |

(52) U.S. Cl.

CPC ................. *A61M 2205/588* (2013.01); *A61M 2205/8206* (2013.01)

(56) References Cited

U.S. PATENT DOCUMENTS

| | | | | |
|---|---|---|---|---|
| 3,521,642 | A | 7/1970 | Jordan | |
| 3,521,643 | A | 7/1970 | Toth | |
| 3,771,534 | A | 11/1973 | Kuehne | |
| 4,094,119 | A | 6/1978 | Sullivan | |
| 4,145,001 | A | 3/1979 | Weyenberg et al. | |
| 4,161,283 | A | 7/1979 | Hyman | |
| 4,284,089 | A | 8/1981 | Ray | |
| 4,480,647 | A | 11/1984 | Sprecker et al. | |
| 4,503,851 | A | 3/1985 | Braunroth | |
| 4,917,301 | A | 4/1990 | Munteanu | |
| 4,947,874 | A | 8/1990 | Brooks et al. | |
| 4,947,875 | A | 8/1990 | Brooks et al. | |
| 5,082,008 | A | 1/1992 | Johnson | |
| 5,167,242 | A | 12/1992 | Turner et al. | |
| 5,301,694 | A | 4/1994 | Raymond et al. | |
| 5,388,594 | A | 2/1995 | Counts et al. | |
| 5,501,236 | A | 3/1996 | Hill et al. | |
| 5,636,787 | A | 6/1997 | Gowhari | |
| 5,799,106 | A | 8/1998 | Mooney et al. | |
| 5,799,663 | A | 9/1998 | Gross et al. | |
| 6,155,268 | A | 12/2000 | Takeuchi | |
| 7,100,618 | B2 | 9/2006 | Dominguez | |
| 7,647,932 | B2 | 1/2010 | Cantrell et al. | |
| 8,430,106 | B2 | 4/2013 | Potter et al. | |
| 8,459,271 | B2 | 6/2013 | Inagaki | |
| 8,997,753 | B2 | 4/2015 | Li et al. | |
| 9,167,852 | B2 | 10/2015 | Xiu | |
| 9,352,597 | B2 | 5/2016 | Sakaino | |
| 9,532,597 | B2 | 1/2017 | Tucker et al. | |
| 9,642,397 | B2 | 5/2017 | Dai et al. | |
| 9,814,262 | B2 | 11/2017 | Peleg et al. | |
| 9,814,263 | B2 | 11/2017 | Cochand et al. | |
| 9,861,772 | B2 | 1/2018 | Terry et al. | |
| 10,172,901 | B2 | 1/2019 | Spencer et al. | |
| 10,278,427 | B2 | 5/2019 | Buchberger | |
| 10,278,927 | B2 | 5/2019 | Hammond et al. | |
| 10,674,771 | B2 | 6/2020 | Buchberger | |
| 10,701,969 | B2 | 7/2020 | Buchberger | |
| 11,116,919 | B2 | 9/2021 | Buchberger | |
| 11,278,052 | B2 | 3/2022 | Mitrev et al. | |
| 11,865,248 | B2 * | 1/2024 | Buchberger | A24F 40/30 |
| 12,070,070 | B2 | 8/2024 | Fraser et al. | |
| 12,186,479 | B2 | 1/2025 | Buchberger | |
| 2004/0221857 | A1 | 11/2004 | Dominguez | |
| 2005/0268911 | A1 | 12/2005 | Cross et al. | |
| 2006/0054155 | A1 | 3/2006 | Bujeau et al. | |
| 2006/0054165 | A1 | 3/2006 | Hughes et al. | |
| 2006/0196518 | A1 | 9/2006 | Hon | |
| 2007/0023056 | A1 | 2/2007 | Cantrell et al. | |
| 2007/0062548 | A1 | 3/2007 | Horstmann et al. | |
| 2007/0074734 | A1 | 4/2007 | Braunshteyn et al. | |
| 2007/0102013 | A1 | 5/2007 | Adams et al. | |
| 2008/0092912 | A1 | 4/2008 | Robinson et al. | |
| 2008/0110458 | A1 | 5/2008 | Srinivasan et al. | |
| 2008/0241255 | A1 | 10/2008 | Rose et al. | |
| 2009/0065011 | A1 | 3/2009 | Maeder et al. | |
| 2009/0272379 | A1 | 11/2009 | Thorens et al. | |
| 2011/0120482 | A1 | 5/2011 | Brenneise | |
| 2011/0226236 | A1 | 9/2011 | Buchberger | |
| 2011/0290267 | A1 | 12/2011 | Yamada et al. | |
| 2011/0297166 | A1 | 12/2011 | Takeuchi et al. | |
| 2012/0204889 | A1 | 8/2012 | Xiu | |
| 2013/0074857 | A1 * | 3/2013 | Buchberger | A24F 7/02 131/329 |
| 2013/0192623 | A1 | 8/2013 | Tucker et al. | |
| 2013/0298905 | A1 | 11/2013 | Levin et al. | |
| 2014/0020693 | A1 | 1/2014 | Cochand et al. | |
| 2014/0166029 | A1 | 6/2014 | Weigensberg et al. | |
| 2015/0245669 | A1 | 9/2015 | Cadieux et al. | |
| 2015/0351456 | A1 * | 12/2015 | Johnson | A24F 40/30 131/329 |
| 2017/0042251 | A1 * | 2/2017 | Yamada | H05B 1/0244 |
| 2017/0095005 | A1 | 4/2017 | Monsees et al. | |
| 2017/0112889 | A1 | 4/2017 | Spencer et al. | |
| 2017/0238611 | A1 | 8/2017 | Buchberger | |

FOREIGN PATENT DOCUMENTS

| | | | |
|---|---|---|---|
| CN | 1323231 | A | 11/2001 |
| CN | 2487392 | Y | 4/2002 |
| CN | 101137446 | A | 3/2008 |
| CN | 101822420 | A | 9/2010 |
| CN | 103393222 | A | 11/2013 |
| CN | 103783674 | A | 5/2014 |
| CN | 1177545 | | 12/2014 |
| DE | 19630619 | A1 | 2/1998 |
| DE | 19654945 | A1 | 3/1998 |
| DE | 102006039115 | A1 | 3/2008 |
| EP | 0150810 | A2 | 8/1985 |
| EP | 0836857 | A1 | 4/1998 |
| EP | 0822760 | B1 | 6/2003 |
| EP | 2481308 | A1 | 8/2012 |
| EP | 2625974 | A1 | 8/2013 |
| EP | 2431808 | B1 | 4/2015 |
| EP | 3180060 | B1 | 1/2019 |
| EP | 3545998 | | 1/2019 |
| GB | 408856 | A | 4/1934 |
| GB | 2488257 | A | 8/2012 |
| JP | S62175896 | U | 11/1987 |
| JP | H0194861 | A | 4/1989 |
| JP | H07184627 | A | 7/1995 |
| JP | H0856640 | A | 3/1996 |
| JP | H119693 | A | 1/1999 |
| JP | 2001507576 | A | 6/2001 |
| JP | 2002078476 | A | 3/2002 |
| JP | 2009502194 | A | 1/2009 |
| JP | 2009509523 | A | 3/2009 |
| JP | 2010506594 | A | 3/2010 |
| JP | 2012507269 | | 3/2012 |
| JP | 2013519382 | A | 5/2013 |
| JP | 2014500472 | A | 1/2014 |
| JP | 2016509852 | A | 4/2016 |
| JP | 2017511703 | A | 4/2017 |
| JP | 2017529896 | | 10/2017 |
| KR | 10-2001-0020746 | | 3/2001 |
| KR | 20010020746 | A | 3/2001 |
| KR | 100483502 | B1 | 4/2005 |
| KR | 10-2007-0087265 | | 8/2007 |
| KR | 20070087265 | A | 8/2007 |
| KR | 10-2008-0059567 | | 6/2008 |
| KR | 20080059567 | A | 6/2008 |
| KR | 20120053521 | A | 5/2012 |
| KR | 20120008751 | U | 12/2012 |

(56) References Cited

FOREIGN PATENT DOCUMENTS

| | | | |
|---|---|---|---|
| KR | 101314934 | B1 | 10/2013 |
| RU | 2297781 | C2 | 4/2007 |
| WO | 8801884 | A1 | 3/1988 |
| WO | 9622801 | A1 | 8/1996 |
| WO | 9828994 | A1 | 7/1998 |
| WO | 03034847 | A1 | 5/2003 |
| WO | 2004089126 | | 10/2004 |
| WO | 2006086655 | A1 | 8/2006 |
| WO | 2007039794 | A2 | 4/2007 |
| WO | 2007042941 | A2 | 4/2007 |
| WO | 2008108889 | A1 | 9/2008 |
| WO | 2009135729 | A1 | 11/2009 |
| WO | 2010045670 | A1 | 4/2010 |
| WO | 2010095659 | A1 | 8/2010 |
| WO | 2010095660 | A1 | 8/2010 |
| WO | 2011109848 | A1 | 9/2011 |
| WO | 2012078973 | A1 | 6/2012 |
| WO | 2013050934 | A1 | 4/2013 |
| WO | 2013083638 | A1 | 6/2013 |
| WO | 2013178769 | | 12/2013 |
| WO | 2014012906 | A1 | 1/2014 |
| WO | 2014016961 | | 1/2014 |
| WO | 2014097294 | A1 | 6/2014 |
| WO | 2014110119 | A1 | 7/2014 |
| WO | 2014140273 | A2 | 9/2014 |
| WO | 2015128499 | | 9/2015 |
| WO | 2016005533 | A1 | 1/2016 |
| WO | 2016024083 | A1 | 2/2016 |
| WO | 2017109448 | A2 | 6/2017 |

OTHER PUBLICATIONS

"Application and File History for U.S. Appl. No. 17/443,170, filed Jul. 21, 2021".
"Application and File History for U.S. Appl. No. 17/452,435, filed Oct. 27, 2021".
"Decision to Grant received for European Patent Application No. 15747202.8, mailed on Jan. 7, 2019".
"Extended European Search Report received for Patent Application No. 19150425.7, mailed on Aug. 26, 2019".
"Intention to Grant received for European Patent Application No. 15747202.8, mailed on Aug. 10, 2018".
"International Preliminary Report on Patentability received for PCT Patent Application No. PCT/AT2011/000122, mailed on Sep. 25, 2012".
"International Preliminary Report on Patentability received for PCT Patent Application No. PCT/GB2015/052212, mailed on Nov. 29, 2016".
"International Search Report and Written Opinion received for PCT Patent Application No. PCT/AT2011/000122, mailed on Aug. 4, 2011".
"International Search Report and Written Opinion received for PCT Patent Application No. PCT/GB2015/052212, mailed on Oct. 21, 2015".
"Mitsubishi Materials Corporation" , available at http://www.mmc.co.jp/corporate/en , Apr. 17, 2018 , 5 pages.
"Multi Flavor Generator", China Academic Journal Electronic Publishing House , 1994-2023 , 3 pages (2 pages of English Translation and 1 page of Official Copy).
"Notice of Allowance received for Chinese Patent Application No. 201910949890.3, mailed on Jan. 3, 2023".
"Notice of Allowance received for Japanese Patent Application No. 2018-239020, mailed on Mar. 26, 2020".
"Notice of Allowance received for Korean Patent Application No. 10-2019-7021114, mailed on Apr. 23, 2021".
"Notice of Reason for Refusal received for Japanese Patent Application No. 2017-507765, mailed on Feb. 4, 2020".
"Notice of Reason for Refusal received for Japanese Patent Application No. 2017-507765, mailed on Jan. 30, 2018".
"Notice of Reason for Refusal received for Korean Patent Application No. 10-2017-7003991, mailed on Apr. 6, 2018".
"Notice of Reason for Refusal received for Korean Patent Application No. 10-2017-7003991, mailed on Oct. 29, 2018".
"Office Action received for Chinese Patent Application No. 201580043507.8, mailed on Nov. 5, 2018".
"Office action received for European Patent Application No. 15747202.8, mailed on Dec. 4, 2017".
"Office Action received for European Patent Application No. 15747208.8, mailed on Dec. 4, 2017".
"Office Action received for Japanese Patent Application No. 2020-078424, mailed on Jun. 29, 2021".
"Office Action received for Korean Patent Application No. 10-2021-7022991, mailed on Oct. 19, 2021".
"Office Action received for Russian Patent Application No. 2017104461, mailed on Apr. 28, 2018".
"Reason for Refusal received for Japanese Patent Application No. 2023-081365, mailed on Jul. 23, 2024".
"Reasons of Refusal received for Japanese Patent Application No. 2018-17006, mailed on Feb. 4, 2020".
"Red Arrow International LLC" , available at www.redarrowinternational.com , Apr. 17, 2018 , 1 page.
"Search Report received for GB Patent Application No. 1414331.7, mailed on Feb. 2, 2015".
Buchberger , "Application and File History for U.S. Appl. No. 13/583,365, filed Oct. 23, 2012".
Buchberger , "Application and File History for U.S. Appl. No. 15/399,121, filed Jan. 5, 2017".
Buchberger , "Application and File History for U.S. Appl. No. 15/503,456, filed Feb. 13, 2017".
Buchberger , "Application and File History for U.S. Appl. No. 16/377,331, filed Apr. 8, 2019".
Celgrad LLC , "World Leader in Battery Separator Technology" , www.celgrad.com , Apr. 17, 2018 , 6 pages.
Freudenberg Vliesstoffe KG , "Vildeon® Filter Mats" , available at http://www.freudenberg-filter.com/company/brands/viledon/ , Apr. 17, 2018 , 2 pages.
Japan Tobacco Inc. , "ZeroStyle®" , available at www.jt.com , Apr. 17, 2018 , 7 pages.
Martin , et al. , "Environmental Tobacco Smoke (ETS): A Market Cigarette Study" , Environment International, vol. 23, No. 1 , 1997 , pp. 75-90.
Mcneil Consumer Healthcare Gmbh , "Nicorette® Inhaler" , available at www.nicorette.de , Apr. 17, 2018 , 8 pages.
Porex Technologies , "Porex Custom Plastics" , available at www.porex.com , Apr. 17, 2018 , 2 pages.
English Translation of Korean Office Action for Korean Patent Application No. KR 2023 7016593 dated Jul. 26, 2025, 5 pages translation, 5 pages original Office Action.
Notice of Reasons for Refusal for Japanese Patent Application No. 2022-196127 dated Dec. 5, 2023, 4 pages translation.
Notice of Reasons for Refusal for Japanese Patent Application No. 2022-196127 dated Sep. 10, 2024 2 pages translation, 4 pages original Notice.
Extended European Search Report, Application No. 25197329.3, dated Oct. 13, 2025, 33 pages.

* cited by examiner

AEROSOL DELIVERY DEVICE AND METHOD UTILIZING A FLAVORING RESERVOIR

RELATED APPLICATION

This application is a continuation application Ser. No. 18/175,933 filed Feb. 28, 2023, which is a continuation application Ser. No. 17/452,435 filed Oct. 27, 2021, now issued U.S. Pat. No. 11,865,248, issued Jan. 9, 2024, which is a continuation of application Ser. No. 17/443,170 filed Jul. 21, 2021, now issued U.S. Pat. No. 12,186,479, issued Jan. 7, 2025, which is a continuation of application Ser. No. 16/842,153 filed Apr. 7, 2020, now issued U.S. Patent No. 11,116,919, issued Sep. 14, 2021, which is a continuation of application Ser. No. 16/377,331 filed Apr. 8, 2019, now issued U.S. Pat. No. 10,674,771, issued Jun. 9, 2020, which is a continuation of application Ser. No. 15/503,456 filed Feb. 13, 2017, now issued U.S. Pat. No. 10,278,427, issued May 7, 2019, which in turn is a National Phase entry of PCT Application No. PCT/GB2015/052212, filed Jul. 31, 2015, which claims priority from GB Patent Application No. 1414331.7, filed Aug. 13, 2014, all of which are hereby fully incorporated herein by reference.

FIELD AND BACKGROUND

The present disclosure relates to an aerosol delivery device and method and in particular but not exclusively to an aerosol delivery device and method that utilise a flavouring reservoir.

An aerosol delivery device can be used for generating a nicotine-containing condensation aerosol.

One example of an inhaler is described in US20110226236 which relates to an inhaler component for producing a nicotine-containing steam/air mixture or/and condensation aerosol by evaporation of a nicotine solution which is highly diluted with ethanol or/and water. The inhaler component comprises the following elements: a housing; a chamber arranged in the housing; an air inlet opening for the supply of air from the surroundings to the chamber; an evaporator for evaporating a portion of the highly diluted nicotine solution, the evaporator comprising an evaporation or steam emission surface arranged in the chamber, from which surface the steam produced passes over to the chamber and mixes in the chamber with the air supplied through the air inlet opening, thereby eventually producing the nicotine-containing steam/air mixture or/and condensation aerosol. In order to remove the high solvent diluent in the formed steam/air mixture or condensation aerosol to a maximum possible extent, the inhaler component comprises a two-step solvent removal device which consists of a condensate drainage and storage device communicating with the chamber and of a condenser through which the produced steam/air mixture or/and condensation aerosol can flow.

Another example of an inhaler component is described in WO2011/109848 which relates to an inhaler component having: a housing with a housing jacket; a mouthpiece with a mouthpiece opening for delivering an inhalable medium into the oral cavity of a user; a scent reservoir that is able to communicate with the environment by diffusion and contains a scent, for releasing the scent into the environment and for the olfactory perception of the scent by the user, wherein a) the housing comprises a housing component; b) the mouthpiece is detachably connected to the housing component; c) the housing jacket comprises a first jacket part and a second jacket part; d) the housing component forms the first jacket part; e) the mouthpiece forms the second jacket part, and f) the scent reservoir is structurally combined with the mouthpiece, has a planar configuration and is arranged flat on the second jacket part or itself forms the second jacket part.

A non-heating type tobacco flavor inhaler is described in WO2010/095659. According to this document, a non-heating type tobacco flavor inhaler is provided with an inhalation holder having an inhalation route defined therein, and also with a filled body disposed in the inhalation route. The filled body consists of tobacco grains, and the inhalation route and the filled body provide air flow resistance in the range from about 40 to about 80 mmAq.

Another non-heating type flavor inhaler is described in WO 2010/095660. According to this document, a non-heating type flavor inhaler provided with: an inhalation holder; an upstream region and a downstream region which are defined in the inhalation holder, said upstream region extending from the tip of the inhalation holder up to a partition wall, said downstream region extending, except the upstream region, from the tip of the inhalation holder up to the mouthpiece end and having a front flow path extending along the upstream region; outside air introducing openings formed in the peripheral wall of the inhalation holder and allowing the upstream region and the outside to communicate with each other; and a pouch mounted at the boundary between the upstream region and the downstream region, extending along the longitudinal axis of the inhalation holder, and releasing the flavor of tobacco.

SUMMARY

Viewed from a first aspect, there can be provided an aerosol delivery device comprising: an air inlet; a flavouring reservoir arranged to provide release of flavouring material to air passing therethrough; and an aerosol chamber arranged to provide an aerosol in air passing therethrough; and an aerosol outlet; the air inlet, flavouring reservoir, aerosol chamber and aerosol outlet are arranged in fluid communication in that order. Thus a flavoured aerosol can be generated in such manner as to avoid a flavouring reservoir becoming contaminated with aerosol particles and/or condensation of liquid from an aerosol, while at the same time providing that the whole air volume of the flavoured aerosol is subjected to both flavouring and aerosol generation.

Viewed from another aspect, there can be provided a device configured to impart flavouring to an airstream admitted the device prior to the airstream reaching an aerosol generator of the device, the device thereby operable to deliver a flavoured aerosol from an outlet. Thus a device can create a flavoured aerosol by passing a whole air volume through both flavouring and aerosol generation without contaminating a flavouring source with aerosol particles and/or condensate.

Viewed from a further aspect, there can be provided a method of generating a flavoured aerosol, the method comprising: imparting flavour to an airflow by passing airflow through a flavour reservoir to cause flavour molecules and/or particles to be carried by the airflow; generating an aerosol by passing the airflow carrying flavour molecules and/or particles through an aerosol generator that evaporates a liquid into the airflow to create a flavoured aerosol; and delivering the flavoured aerosol to a mouthpiece. Thus a flavoured aerosol can be generated in such manner as to avoid a flavouring reservoir becoming contaminated with aerosol particles and/or condensation of liquid from an aerosol, while at the same time providing that the while air volume of the flavoured aerosol is subjected to both flavouring and aerosol generation.

BRIEF DESCRIPTION OF THE FIGURES

The present disclosure will now be discussed, by way of example only, with reference to the following drawings in which like reference numerals denote like elements.

Figure 1:
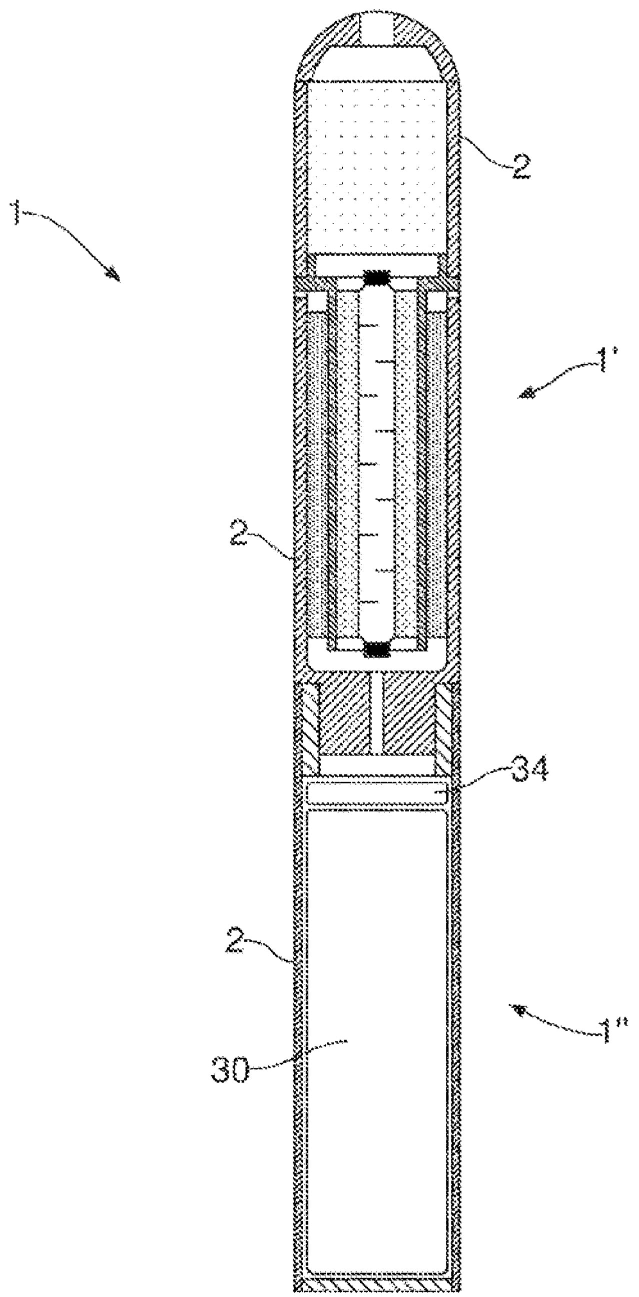
FIG. 1 shows a cross-sectional side view of an aerosol delivery device comprising an aerosol-forming member according to a first example.

While the presently described approach is susceptible to various modifications and alternative forms, specific embodiments are shown by way of example in the drawings and are herein described in detail. It should be understood, however, that drawings and detailed description thereto are not intended to limit the scope to the particular form disclosed, but on the contrary, the scope is to cover all modifications, equivalents and alternatives falling within the spirit and scope as defined by the appended claims

DESCRIPTION

Referring to FIG. 1, there is shown a first example of an aerosol delivery device. The aerosol delivery device 1 comprises an aerosol delivery portion 1' and a power portion 1". In the present example, the aerosol delivery portion 1' and power portion 1" are arranged as separate regions of a single, unitary, aerosol delivery device 1 having a single housing 2 that houses both portions. In other examples, the aerosol delivery portion 1' and power portion 1" can be removably connected to enable a given power portion 1" to receive a number of different aerosol delivery portions 1' and/or to enable a given aerosol delivery portion 1' to receive a number of different power portions 1". In such alternative examples, the housing 2 may be openable to enable replacement of one portion or may be divided in correspondence to the division of the portions such that each portion includes its own respective housing part.

The aerosol delivery device 1 may be configured to be re-usable or disposable. In the example in which the aerosol delivery portion 1' and power portion 1" are separable, either or both of the aerosol delivery portion 1' and power portion 1" may be configured as being re-usable or disposable.

The power portion 1" provides a source of electrical power for powering one or more components within the aerosol delivery portion 1'. In the present example, the power portion 1" has with the housing a battery 30. Delivery of power from the battery 30 to the aerosol delivery portion 1' is controlled by electric circuitry 34. In other examples the battery may be replaced by another portable power source such as a capacitive power store such as a supercapacitor or ultracapacitor, a mechanical power source such as a spring or dynamo, or an alternative chemical energy source such as a fuel cell.

Figure 2:
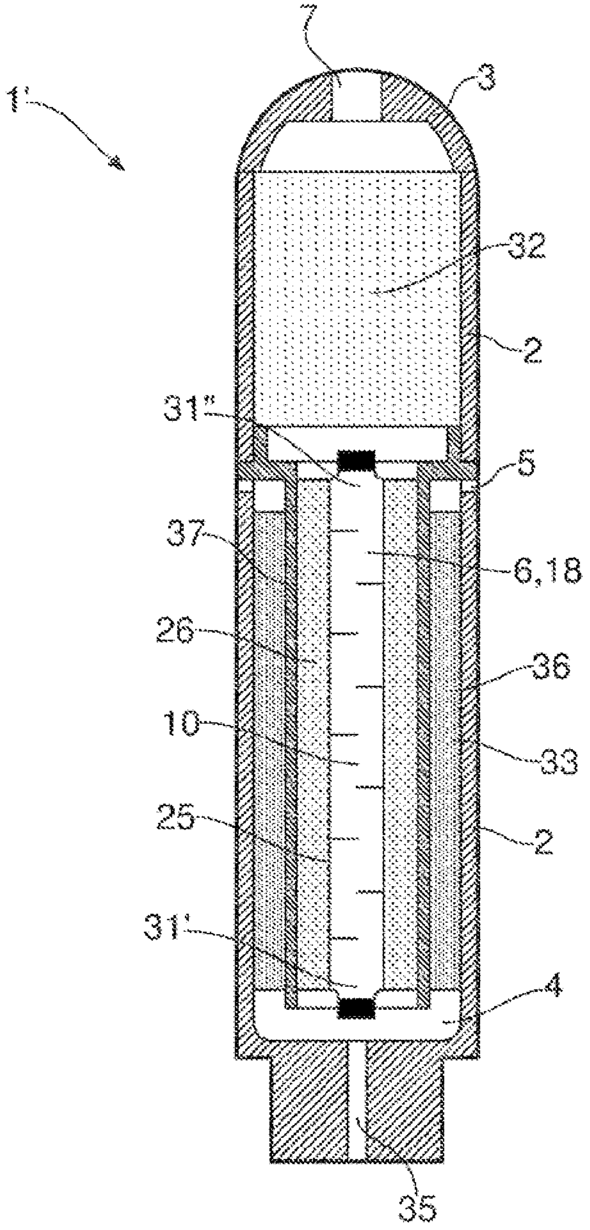
FIG. 2 shows a cross-sectional side view of an aerosol delivery portion of the aerosol delivery device shown in FIG. 1.

FIG. 2 shows the aerosol delivery portion 1' in greater detail. As can be seen from FIG. 2, the aerosol delivery portion 1' is contained within housing 2 and has a mouthpiece 3 at one end and an attachment element at the other end. The attachment element is configured to connect (either permanently or releasably) to the power portion 1". As shown in FIG. 2, the attachment element has a connection member 35 to provide for electrical connection between the power portion 1" and any power utilising elements of the aerosol delivery portion 1'.

The aerosol delivery portion 1' as shown in FIG. 2 defines a gas pathway therethrough, the gas pathway having an inlet 5, a flavouring reservoir 36, a plenum chamber 4, an aerosol chamber 6 (also referred to as tubular channel 18), refining member 32 and an outlet aperture 7 that extends through the mouthpiece 3. Air can be encouraged to flow through the gas pathway by the application of suction at the mouthpiece 3. Such suction may typically be provided by a user drawing air through the aerosol delivery device 1 when inhaling to receive a delivery of aerosol. In overview, air taken in through the inlet 5 and passing along the gas pathway first picks up flavouring material from the favouring reservoir 36 before the forming of an aerosol at the aerosol chamber 6 for delivery to the outlet aperture 7. This process will be described in more detail below.

As shown in FIG. 2, the flavouring reservoir 36 provides an inlet passage or channel between the inlet aperture 5 and the plenum chamber 4. In some examples a single inlet 5 may be provided and in other examples a number of inlets 5 may be provided at different points around the circumference of the housing 2. The inlet passage or channel provided by the flavouring reservoir has an annular cross section and encompasses the aerosol chamber 6 and associated aerosol forming member 10. In the configuration of the present example, the air inside the inlet passage and the aerosol inside the tubular channel 18 (aerosol chamber 6) are flowing in opposite directions.

As fresh air moves through the inlet passage it passes over or through the flavouring reservoir 36 which results in the release of flavours. The flavours disperse in the air and are taken downstream together with the air. The flavour enriched/flavoured air is then collected in the plenum chamber 4. The plenum chamber 4 acts to provide uniformity to the flow of air to the aerosol chamber 6/tubular channel 18. The air enters the aerosol chamber 6 via an air inlet 31'.

As will be described in more detail below, the aerosol forming member 10 has a chamber wall 25 surrounding the aerosol chamber 6, then a liquid reservoir matrix 26 is arranged outside the chamber wall, with the aerosol chamber 6 having an aerosol chamber inlet 31' and an aerosol chamber outlet 31". Separation between the inlet passage/flavouring reservoir 36 and the liquid reservoir matrix 26 is provided by a support member 37 located between the liquid reservoir matrix 26 and the flavouring reservoir 36. The aerosol forming member 10 uses heat provided by the flow of electrical current to aid the aerosol generation.

In the present example, the flavouring reservoir 36 is located around the aerosol forming member 10. While the heat generated by the heating element of the aerosol forming member 10 is primarily used to vaporise liquid provided from the liquid reservoir matrix 26, a portion of that heat may be used to heat up the flavouring reservoir 36 to an elevated temperature. This secondary or waste heat can be transferred to the flavouring reservoir by thermal conduction through components of the aerosol forming member 10 and support member 37. For example, heat may be conducted through the chamber wall 25, through the liquid reservoir matrix 26 and through the tubular support member 37 holding the aerosol forming member 10 and the liquid reservoir matrix 26, and thereby provided to the flavouring reservoir 36 and the flavours contained therein.

This conductive heat transfer enables the flavouring reservoir 36 to reach temperatures that it would not reach otherwise, enabling enhanced release of flavours inside the reservoir. As the release of flavours inside the reservoir is principally by diffusion, and as diffusion is significantly temperature dependent in operation, the amount of temperature elevation achieved in the flavouring reservoir by the conductive heat transfer need not be large to achieve the enhanced release of flavours. In addition to the thermal conductivity properties of the conductive heat transfer path and a heated structure of the reservoir, the amount of temperature rise may depend upon a number of factors associated with use of the device. For example the length of a given draw or puff through the device may affect the operating time of the heating element and thus the total amount of heat generation that occurs during the draw or puff. Also, the time space between draws or puffs may impact the total temperature rise if that timespan is sufficiently short that at least some components of the device do not cool fully between draws or puffs. In practice a temperature rise on the range of 5° C. to 30° C. is anticipated to be feasible and a rise of as little of 1° C. is expected to provide some enhancement to the release of flavours. For a given implementation of the device, an expected temperature rise can be calculated and measured and in some examples it may be appropriate to tailor the flavours in the flavouring reservoir to the expected temperature rise.

The arrangement of the present example provides that the only gas to enter the flavouring reservoir is air introduced into the device via the inlet aperture(s) 5. Since the flavouring reservoir 36 does not receive vapour or aerosol generated inside the aerosol chamber 6, the surface of flavour providing elements within the flavouring reservoir will not attract or become clogged with condensate or aerosol particles generated at the aerosol chamber 6.

As will be appreciated, the entire air volume drawn in by a user when inhaling to receive a delivery of aerosol (which volume may typically be of the order of 30-80 ml) is provided to the aerosol chamber 6 and can completely be used for generating the aerosol. This can provide for efficient aerosol formation.

The flavouring reservoir 36 may comprise a permeable highly porous wadding or filling material. In the present example, the material completely fills/extends over the channel cross section of the inlet passage or channel in which the flavouring reservoir 36 is arranged. In other examples, the flavouring reservoir 36 may extend over a portion that is less than the whole cross section. The flavouring reservoir 36 may consist of a prefabricated pack or cartridge. In some examples, the flavouring reservoir may comprise or consist of tobacco or tobacco extract. Suitable tobaccos are, in particular, dried fermented tobacco, reconstituted tobacco, expanded tobacco or mixtures of the same. The tobacco may be present as cut tobacco, such as fine cut tobacco, or as fine granulates or tobacco flour. Such forms provide a relatively large surface area to facilitate the release of flavours contained in the tobacco. In another example, the flavouring reservoir 36 may comprise an inert wadding or filling material or another open-pored inert substrate, the surface of which is coated with a flavouring material. The coating may, for example, contain an extract, condensate or distillate of tobacco or tobacco smoke, or a fraction such as a volatile, aromatic or flavourful fraction of the aforementioned extracts, condensates or distillates, or tobacco flour. Any material, such as the examples given above, of a flavouring extracted from or based upon, at least in part, tobacco may be termed a tobacco derivative. The coating can alternatively or additionally contain menthol or an essential oil.

The flavouring substance or material can be a substance insoluble in water and/or glycerol. In the present context, insolubility is indicative of a solubility of less than one percent by weight at 20° C. and 1 atm. Thus, by providing for dispersal of flavourings into the airflow within the flavouring reservoirs, even flavourings that are not water or glycerol soluble can be effectively included in the aerosol provided by the aerosol delivery device.

Thereby a flavouring can be provided to the air entering through the inlet 5. As described above, the release of flavour to the passing air can be facilitated or assisted by heating of the flavouring reservoir, for example using the approach of conducting excess heat from the aerosol forming device 10 to the flavouring reservoir 36.

In the present example, the flavouring reservoir 36 is additionally configured as a flow resistor 33. The flow resistor 33 provides the main pressure drop when a user is drawing in air (inhaling through the device, also referred to as drawing on the device or puffing on the device). The arrangement of the flow resistor can be configured to provide a level of pressure drop appropriate to a particular intended use. In one example, the pressure drop can be configured to correspond to or approximate the pressure drop that would be expected of a conventional (i.e. ignited tobacco type) cigarette. The comparatively large volume of the flavour reservoir 36 can provide flow characteristics that substantially correspond to those of a cigarette. In other examples where the device is configured for delivery of flavouring and/or liquid suspension in aerosol of materials other than those associated with tobacco smoking, an alternative pressure drop may be configured as required for the intended use. The flow characteristics of the arrangement depicted in FIG. 2 are substantially linear, i.e. the pressure drop over the flavouring reservoir 36 is directly proportional to the flow rate through the flavouring reservoir 36.

Figure 3:
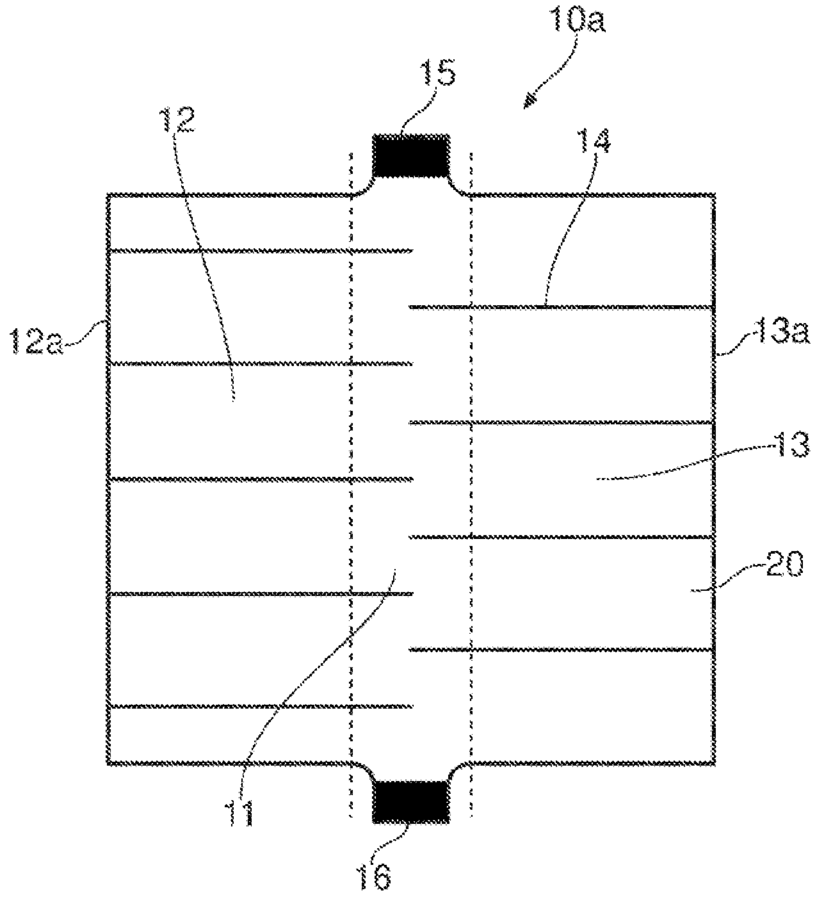
FIGS. 3 to 7 show example aerosol forming members.

FIG. 3 now shows more detail of the aerosol forming member. As shown in FIG. 3, an aerosol-forming member **10*a* comprises a material that is configured to wick and heat a solution such that the sheet of material can absorb solution and thereafter heat it up such that it evaporates and forms a vapour. The material used in the present examples is sheet-like in nature and comprises two major opposing surfaces 20, 21. The sheet of material may comprise an open-pored structure, foam structure or interconnecting network of pores, all of which form a capillary structure. The capillary structure enables the aerosol-forming member 10*a*** to wick or absorb a solution. The term “capillary structure” used herein is to be understood as a structure through which liquid or a solution can travel as a result of capillary action.

The aerosol-forming member **10*a* of the present example may be made of a porous, granular, fibrous or flocculent sintered metal(s) so as to form a capillary structure. For instance, Bekipor™ sintered fibre material from Bekaert (www.bekaert.com) falls in this category of materials. In other examples, the aerosol-forming member 10*a* comprises an open-pored metallic foam or a group of layers of wire mesh or calendered wire mesh which also form capillary structures. The aerosol-forming member 10*a* may be formed from stainless steel. Furthermore, the aerosol forming member 10*a* may be formed with a capillary structure that extends throughout the whole aerosol-forming member 10*a*** such that it is exposed on the two major surfaces 20, 21 of the sheet of material. In some examples, one of the major surfaces 20, 21 may be sealed with a metallic foil or cover that is sintered or attached to said major surface. Alternatively, a region of one or both of the major surfaces 20, 21 may be sealed. In another example, the aerosol-forming member 10*a* is configured such that the capillary structure does not extend throughout the whole aerosol-forming member. In another example, a thin support layer may be sintered onto one or both of the major surfaces 20, 21. Such a support layer may be formed from a wire mesh made of stainless steel.

The material from which the aerosol-forming member 10*a* is formed is heatable in that it comprises sufficient electrical resistivity so that when current is passed through, the aerosol-forming member 10*a* heats up to a temperature sufficient to cause the solution held in the capillary structure to evaporate or vaporise. Therefore, in the present examples, the aerosol-forming member 10*a* can be considered to comprise a heating element formed with a capillary structure such that the heating element and the capillary structure are integrated and form a single entity or unit.

In the above described examples wherein the sheet of material comprises a single layer configured to wick and heat a solution, the sheet of material can be described as comprising a heating element and a wick that are arranged in the same surface.

Additionally, the aerosol-forming member 10*a* may comprise any combination of the aforementioned structures and materials, e.g. by providing multiple layers of different structures/materials, the layers being joined together, e.g. by sintering.

In one such example, the aerosol-forming member comprises a sheet of material that is sheet-like in nature and formed from a plurality of layers. For example, the aerosol-forming member 10*a* may comprise a first heatable layer acting as a heating element. This first layer is formed from a material that is configured to be heated up. This first layer may be formed from a metal, such as stainless steel. The aerosol-forming member 10*a* may further comprise a second layer formed with an open-pored structure, foam structure or interconnecting network of pores, all of which form a capillary structure. The capillary structure enables the aerosol-forming member 10*a* to wick or absorb a solution. This second layer may be made of a porous, granular, fibrous or flocculent material so as to form the capillary structure. Alternatively, the second layer may comprise an open-pored foam, fabric or a group of mesh layers forming the capillary structure. The second layer may be made of a non-conductive material such as glass, carbon or ceramic. This second layer acts as a wick. The first layer (heating element) and the second layer (wick formed with a capillary structure) are laid on top of each other so as to form a sheet of material having two opposing major surfaces, wherein the capillary structure may be exposed on one or both of the major surfaces. In this example, the sheet of material can be described as comprising a heating element and a wick arranged in parallel surfaces. In one example, the first layer may be formed of a metal wire mesh or metal foil and the second layer may be formed of a glass fibre structure or fabric fritted onto or otherwise attached to the first layer.

In another example, the first layer also comprises a capillary structure as described above with reference to the second layer, such that the first layer can both heat and wick a solution. In this example, the sheet of material can be described as comprising a heating element and a wick that are arranged in the same surface and in parallel surfaces.

In another example, the sheet of material comprises a third layer that is similar to the second layer in that it comprises a capillary structure. The second and the third layer sandwich the first layer such that the capillary structure is exposed on both major surfaces of the sheet of material.

The sheet of material according to any of the above described examples has a thickness or depth that typically falls within the range of 20-500 μm. In some examples, the thickness falls within the range of 50 to 200 μm. The thickness or depth should be understood as meaning the distance between the two major surfaces 20, 21 of the sheet of material.

Figure 4:
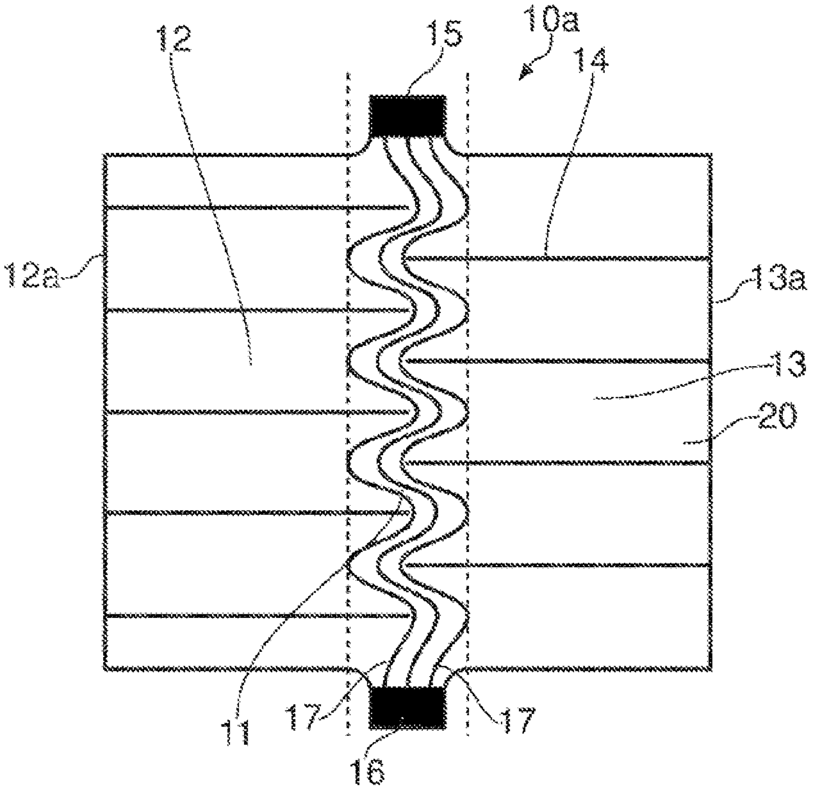
Figure 6:
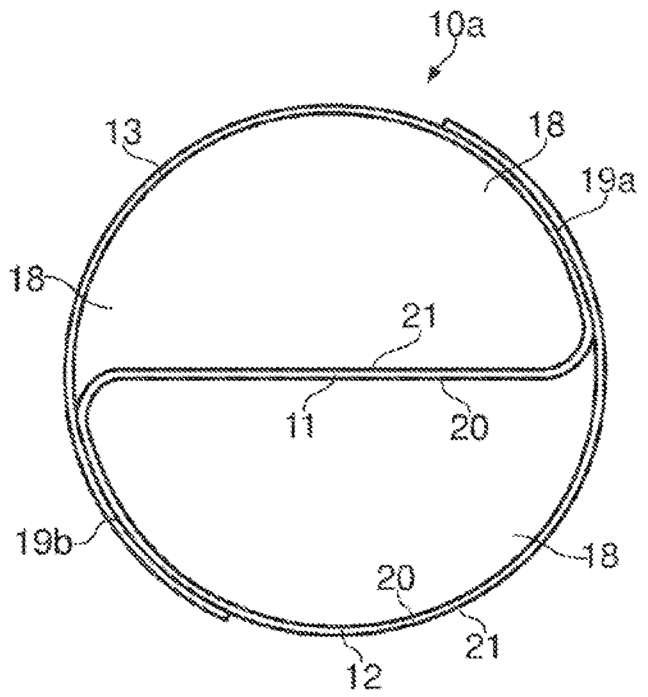

FIGS. 3 and 4 show the aerosol-forming member 10*a* in an unfolded state or position and FIG. 6 shows the aerosol-forming member 10*a* in a folded state or position. The sheet of material has a first or central section 11 and a second and a third section 12, 13 on either side of the central section 11. The dashed lines in FIG. 3 represent the boundaries between the sections 11, 12, 13. The second 12 and third 13 sections are formed with slots or notches 14 that extend from opposing long edges 12*a*, 13*a* of the aerosol-forming member 10*a* towards and into the first section 11. In the arrangement shown in FIG. 3, the second section 12 is formed with five slots 14 and the third section 13 is formed with four slots 14, although other configurations of numbers of slots are possible. The slots 14 as illustrated in FIG. 3 are approximately parallel to one another and spaced apart across the second and third sections 12, 13.

Opposing free ends of the first section 11 act as electrical terminals 15, 16. The electrical terminals 15, 16 are configured to be electrically connected, e.g. via an electric circuitry 34, to a power source, such as the battery 30, so that an electric current can be passed across the aerosol-forming member 10*a*. The electrical terminals 15, 16 may extend from the first section as seen in FIG. 2 enabling them to slot into connection holes (not shown) of the aerosol delivery device, the connection holes being electrically connected to the power source. Alternatively, an electrically conductive wire connected to the power source may be clipped, soldered or welded onto each electrical terminals 15, 16 so that a current can be passed across the aerosol-forming member 10*a*. In some examples, the electrical terminals are in line with adjacent edges of the second and third sections 12, 13 such that the terminals do not protrude. These terminals may be connected to an electrically conductive wire via a clip and/or the wire may be soldered or welded onto the terminals. It should also be understood that the electrical terminals may be of any other shape and it is envisaged that other means suitable for connecting the electrical terminals to the power source may be used.

When a current is passed through the aerosol-forming member 10*a*, the slots 14 compress the electric field 17 such that it is substantially contained within the first section 11 as illustrated in FIG. 4. The dashed lines in FIG. 4 represent boundaries between the first, second and third sections 11, 12, 13. As a result, the first section 11 is primarily or directly heated up whilst the second and third sections 12, 13 remain relatively unheated, although some heat generated by the current passing through the first section is expected to cause some heating of the second and third sections 12, 13. Heat that is generated in or which is conducted to the second and third sections can then be onwardly conducted to provide a small level of heating to the flavouring reservoir 36 as described above. Additionally or alternatively heat may be transferred to the flavour reservoir by one or more of radiation heat originating from the heated first section 11 and absorbed by the chamber wall, and condensation heat released from vapour condensing on chamber wall 25. The heat transferred to the flavouring reservoir can be thought of as secondary heat or waste heat as such heat is not directly used for generating the aerosol.

Figure 5:
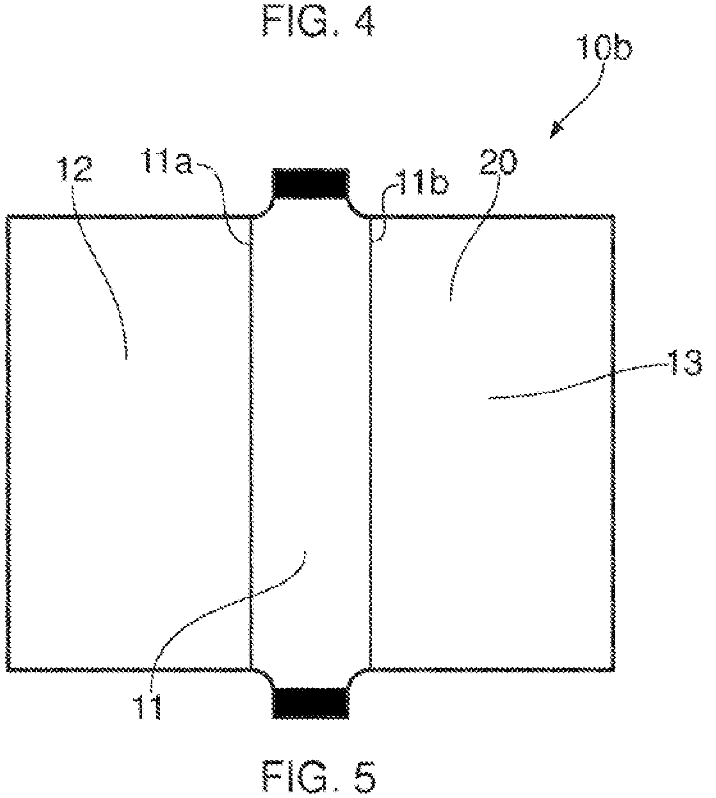

The present teachings are however not limited to an aerosol-forming member 10*a* comprising slots so as to contain the heat within the first section 11. An example of such an arrangement is shown in FIG. 5, where the sheet of material comprises discrete sections with different material properties. The first section 11 is made of a material of low electrical resistivity whereas the second or the third sections 12, 13 are formed from a material with high electrical resistivity such that when a potential difference is applied between the terminals 15, 16, an current will primarily pass through the first section. It should be understood that the first section may also be formed with a capillary structure such that it extends throughout the whole aerosol-forming member. The difference in electrical resistivity results in that the first section 11 heats up relatively to the second and third sections 12, 13.

An example of such an embodiment is wherein the sheet of material comprises a non-conductive fibre web or fabric made of glass or carbon fibres, glass or carbon fibre yarns or any other non-conductive and inert fibre materials. The fibre web or fabric provides the capillary structure and extends throughout all sections of the sheet of material. Conductive fibres or wires are incorporated in the fibre web or fabric in a first or central section of the sheet of material making said first or central section heatable. The conductive fibres or wires may be made of stainless steel or of a heating wire alloy like Chromium Nickel. Alternatively, conductive fibres may replace non-conductive fibres and conductive wires (heating wires) may replace non-conductive yarns.

Thus it will be understood that a variety of constructions consistent with the present teachings are possible to achieve primary heating of a first section 11 to facilitate aerosol generation and to achieve secondary heating by way of conduction of heat from the aerosol forming member to the flavour reservoir.

Referring now to FIG. 6, there is shown the aerosol-forming member 10*a* in a folded state or position. The second and third sections 12, 13 are folded about the first section 11 such that the second and third sections 12, 13 enclose the first section 11 and form a channel 18. Regions 19*a*, 19*b* of the second and third sections 12, 13 overlap such that the channel 18 is completely enclosed in a direction about the first section 11. The first section 11 is substantially planar or flat and suspended in the channel 18 such that it extends across the channel 18.

It should be understood that the second and third sections 12, 13 do not have to form a tubular channel 18. In alternative examples the second and third sections 12, 13 are folded about the first section 11 such that they form a channel having an oval, square, rectangular or any other type of polygonal cross-section.

Figure 7:
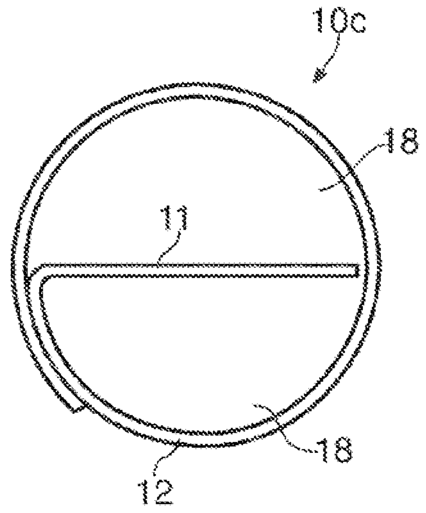

It should also be appreciated that the first section 11 is not limited to being planar or flat. In an alternative example, the first section 11 comprises corrugations having ridges and grooves such that it follows a meandering or oscillating path, or a sinusoidal curve. The ridges and grooves may extend in a direction parallel to the opposing long edges 12*a*, 13*a* of the sheet of material. In another example, as shown in FIG. 7, the third section 13 is omitted such that the aerosol-forming member 10*c* has a first section 11 and a second section 12. The second section 12 extends from the first section 11 and folds about the first section 11 such that the second section 12 forms a channel 18 and the first section 11 is suspended across the channel 18. Alternatively, the second section 12 partially encloses the first section 11. For example, the second section 12 may extend around a single surface of the first section such that the cross-section of the aerosol-forming member has a semi-circular shape.

Figure 8:
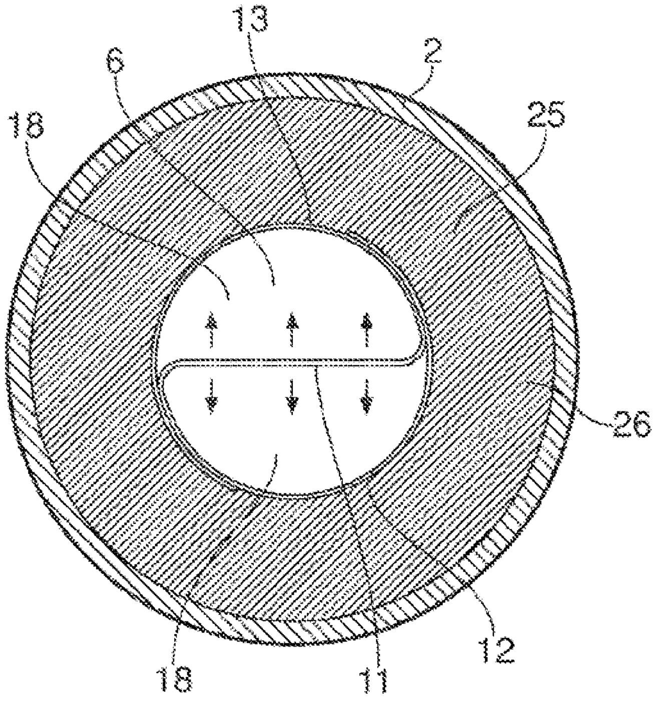
FIG. 8 shows an example aerosol-forming member located in an aerosol chamber.

Referring now to FIG. 8, the aerosol-forming member 10*a* is located in the aerosol chamber 6. The aerosol forming member thus defines the chamber wall 25 adjacent or proximal a liquid reservoir matrix. The chamber wall therefore may be expected to be at a boundary edge of the structure making up the reservoir matrix. The liquid reservoir matrix 26 comprises a capillary structure, for example an interconnecting porous or open-porous structure, such that it can hold a solution or liquid. The liquid reservoir matrix 26 may be formed from a fibre material, for example polyethylene or polyester fibres. In an example where heat is to be provided to the flavouring reservoir 35 by conduction of secondary heat from the aerosol forming member, the liquid reservoir may be configured to provide conduction of the secondary heat. This may be provided by the reservoir matrix itself being thermally conductive or may be provided by thermally conductive elements passing through or around the reservoir matrix.

The shape of the aerosol chamber 6 defined by the chamber wall 25 corresponds to the shape of the aerosol-forming member 10*a*. In the arrangement shown in FIG. 8, the second and third sections 12, 13 contact the liquid reservoir matrix 26. In other examples, it may be that only one of the second and third sections 12, 13 contacts the liquid reservoir matrix 26. Alternatively, if the aerosol-forming member only comprises a second section 12 as seen in FIG. 7 then only the second section is in contact with the liquid reservoir matrix 26. It should also be understood that it is not necessary for the whole second and/or third sections 12, 13 to contact the liquid reservoir matrix 26. For example, only a portion of the second and/or third sections may contact the liquid reservoir matrix 26. In such examples it may be the case that surface sections of the liquid reservoir matrix 26 (not in contact with sections 12, 13) effectively form sections of the chamber wall 25. In another example the aerosol-forming member 10*a* may contact the liquid reservoir matrix 26 only via the outer edges of sections 12, 13. In this example the chamber wall 25 is completely formed by the liquid reservoir matrix 26.

As will be appreciated, the aerosol forming chamber and aerosol forming member may be constructed in any appropriate manner that provides for aerosol formation as air passes through a chamber. Thus as an alternative, so-called atomisers based upon use of a heating coil wound around a fibre wick may be used.

As is illustrated in FIG. 8, the first section 11 is located across the aerosol chamber 6. Advantageously, the liquid reservoir matrix 26 does not have to be made out of a heat resistant material as it is shielded from the heat of the first section 11 by the second and/or third sections 12, 13 that are not substantially heated up during operation of the aerosol delivery device 1. The secondary heat conducted through or across the reservoir matrix is of sufficiently small magnitude that special thermal resistance is not expected to be required.

The liquid reservoir matrix 26 holds a solution that is formed into aerosol by the aerosol-forming member 10*a*. The solution is drawn or absorbed into the aerosol-forming member 10*a* by capillary action via the capillary structure of the second and the third sections 12, 13. The solution is spread throughout the capillary structure of the aerosol-forming member 10*a*, i.e. the first, second and third sections 11, 12, 13. When the first section 11 is heated up, the solution evaporates from the first section 11 so as to form a vapour which upon condensation forms an inhalable aerosol. Thereafter, and even during the heating, the first section 11 is replenished with solution by capillary action moving solution from the liquid reservoir matrix 26, via the second and third sections 12, 13 to the first section 11. This is described in more detail below.

The capillarity of the aerosol-forming member 10*a* may be greater than the capillarity of the liquid reservoir matrix 26 so as to induce flow of solution from the liquid reservoir matrix 26 towards the aerosol-forming member 10*a*. The capillarity is defined by the pore size and the wetting conditions of the respective capillary structures.

As previously described, the power source enabling the aerosol-forming member 10*a* to heat up may be a battery 30. The battery 30 is controlled by the electric circuitry 34 which include a controller and may be mounted on a printed circuit board (PCB). Examples of illustrative circuit structures are shown in FIGS. 9*a* and 9*b*.

Figure 9A:
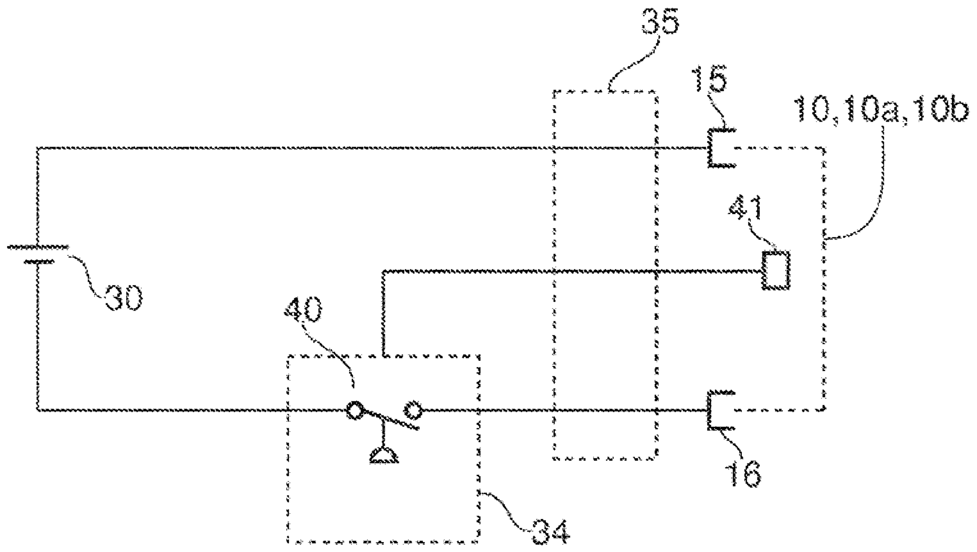
FIGS. 9*a* and 9*b* show example control circuits.

As is shown in FIG. 9*a*, the electrical terminals 15, 16 of the aerosol-forming member 10*a* are electrically connected to the positive and negative terminals of the battery 30 respectively as previously described. Control of electrical current to the terminals 15, 16 is provided by the electrical circuit 34. The circuit of this example includes a pressure-activated switch 40 that activates responsive to a signal from a pressure sensor 41. The pressure sensor 41 is arranged to detect a pressure alteration when a user commences inhaling through the aerosol delivery device. The pressure sensor may for example be arranged in fluid communication with the plenum chamber 4 in order to detect the pressure change. Although it is indicated in FIG. 9 that the pressure sensor 41 is connected to the electric circuit 34 via the connection member 35, it is also possible to arrange the pressure sensor 41 at the electric circuit 34 and to provide fluid communication between the plenum chamber 4 and the pressure sensor 41 via a passage extending through the connection member 35. The signal from the pressure sensor 41 then activates the switch 40 (either directly or via a controller) so as to allow a flow of current from the battery 30 to the terminals 15, 16. The switch 40 may be an electrical switch such as a power-MOSFET switching circuit activatable responsive to the signal from the pressure sensor. The switch and any control circuitry therefor may be provided at a PCB of the electric circuit 34.

Figure 9B:
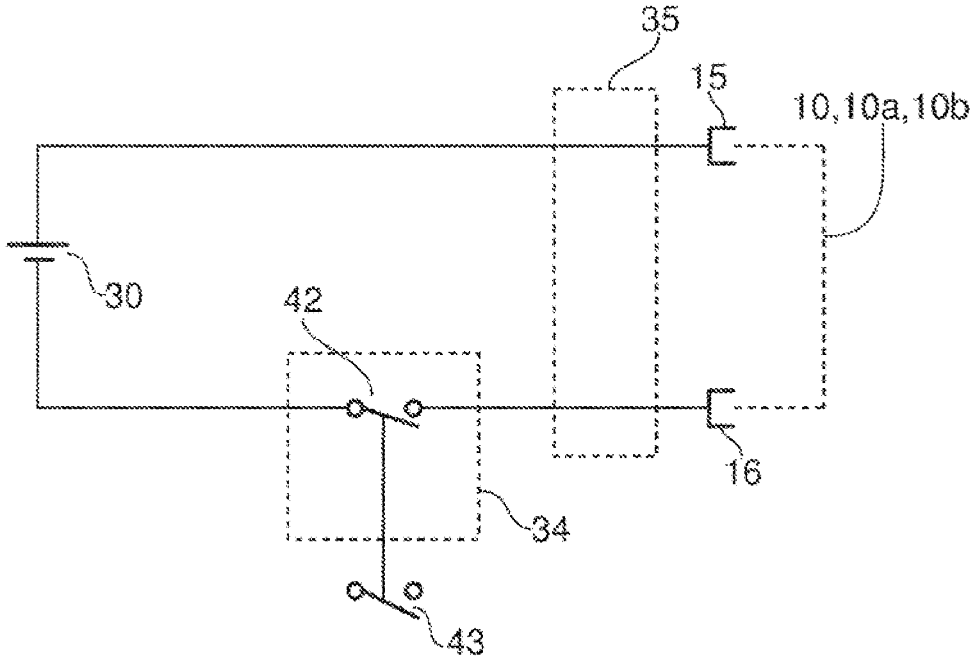

As shown in the example of FIG. 9*b*, the control of the supply of current from the battery 30 to the terminals 15, 16 may be controlled via a switch 42 that activates responsive to a user-activated switch 43. The user-activated switch may be located at an accessible position on or recessed into the housing 2. The switch 42 may be activated based upon a direct connection to the user-activated switch 43. Alternatively, a control circuit may be provided to control the switch 42 responsive to activation of the user-activated switch 43. The switch 42 may be an electrical switch such as a power-MOSFET switching circuit activatable responsive to the signal from the user-activatable switch 43. The switch and any control circuitry therefor may be provided at a PCB of the electric circuit 34.

In addition, the switching circuit may additionally provide automatic control of the temperature, for example, by using temperature sensors to enable the supply of current to be stopped once a threshold temperature is reached. The switching circuit may additionally or alternatively provide automatic control of duration, to enable the supply of current to be stopped once a threshold activation time is reached.

In some examples, the circuit 34 may be configured to very low or zero power requirements other than when the switch is activated to indicate that provision of current to the terminals 15, 16 is required.

When current is drawn from the battery 30 and through the sheet of material, the electrical resistance of the sheet of material causes the first section 11 of the sheet of material to increase in temperature. In the embodiment wherein the sheet of material comprises several layers, the resistance of the conductive layer acting as a heating element causes the first section 11 to increase in temperature, which in turn heats up the adjacent non-conductive second and/or third layers of the first section 11.

Operation of the aerosol delivery device 1 will now be described with reference to FIGS. 1 and 8. In use, the user may manually activate the aerosol delivery device 1 (for example see the arrangement of FIG. 9*b*) or the aerosol delivery device 1 may be activated automatically (for example see FIG. 9*a*) as the user starts to inhale through the aerosol delivery device 1. In either approach, the battery 30 provides a potential difference between the electrical terminals 15, 16 of the aerosol-forming member 10*a* as the aerosol delivery device is activated, causing current to flow between the electrical terminals 15, 16 such that the first section 11 of the sheet of material increases in temperature. The heat is substantially contained within the first section 11 due to the slots 14, although it should be appreciated that the heat may be contained within the first section by other means as described above. It will also be appreciated that secondary heat may be conveyed to the flavouring reservoir 35 as described above. This increase in temperature at the first section 11 causes the solution held in the capillary structure of the first section 11 of the sheet of material to evaporate so as to form a vapour. The vapour mixes with air drawn into the aerosol delivery device 1 via inlet 5, flavouring reservoir 35, plenum chamber 4 and chamber inlet 31' by suction caused by a user inhaling through the device. The vapour mixes with air in the aerosol chamber 6, and as this occurs the vapour condenses and forms droplets such that an inhalable aerosol is produced.

The aerosol-forming member 10*a* according to any of the above described embodiments is located in the housing such that the planes of the major surfaces 20, 21 are parallel to or substantially aligned with the direction of the airflow through the aerosol chamber 6. Thus, when a solution is held in the aerosol-forming member 10*a* and it is heated up such that the solution evaporates, the solution evaporates in a direction transverse to the direction of the airflow. In the embodiments wherein the capillary structure is exposed on both sides of the sheet of material, the solution is evaporated from both sides in opposite directions as indicated by the arrows in FIG. 8. The vapour mixes with air so as to form aerosol in the channel 18 formed by the second and/or third sections 12, 13. The channel 18 directs the flow of aerosol through the aerosol delivery device towards the user.

When the aerosol forming device is activated, it is likely that excess vapour will form and then condense onto the chamber wall 6 formed by the second and/or third sections 12, 13 of the aerosol-forming member 10*a*. The condensation heat released may thus provide a source of heat for transfer to the flavour reservoir; the condensate will be reabsorbed into the capillary structure of sections 12, 13 and resupplied to section 11 of the aerosol-forming member 10*a* by capillary action as discussed above. In addition to any such condensation heat, the supply of secondary or waste heat to the flavour reservoir may also be provided by conductive heat transferred within the aerosol forming member from the high temperature section 11 to the adjacent cooler sections 12, 13. Further, the supply of secondary or waste heat to the flavour reservoir may also be provided by radiation heat transferred from the high temperature section 11 to the adjacent cooler sections 12, 13. Heat rays can cross the aerosol chamber 6 and are then absorbed on the chamber wall 25 formed by sections 12, 13. All three sources of heat together are expected to be active to some extent, with the relative ratio therebetween being dependent upon the exact device configuration. Together these mechanisms provide the secondary or waste heat. This waste heat is passed through or around the liquid reservoir matrix 36 so as to reach the flavouring reservoir 36 for heating the flavouring contained therein.

After the aerosol-forming member 10*a* has been activated and aerosol has formed in the channel 18, the aerosol is drawn through the channel 18 as the user continues to inhale. The aerosol then exits the aerosol chamber 6 through a chamber outlet 31" as seen in FIG. 2. The aerosol then passes through an optional aerosol refining member 32 provided in the housing 2, causing the aerosol to be cooled. The refining member 32 may also contain further flavouring agents such as menthol that are released into the flow of aerosol before entering the user's mouth via the outlet aperture 7 provided in the mouthpiece 3. Meanwhile, the solution that has evaporated from the capillary structure of the first section 11 of the sheet of material is replaced by fresh solution from the liquid reservoir matrix 26 due to the capillary effect of the capillary structure as described above and the second and/or third section being in contact with the liquid reservoir matrix 26. Fresh air enters the channel 18 via the inlet aperture 5, flavouring reservoir 36, plenum chamber 4 and chamber inlet 31'. In some examples, a pressure drop element or flow resistor 33 is provided so that the flow of air into the aerosol chamber 6 can be controlled. The flow resistor 33 may consist of a simple aperture or hole and may be identical with the inlet aperture 5 in the housing 2. Alternatively the flow resistor 33 may consist of a porous body similar to a cigarette filter providing the flow resistance of a conventional cigarette. In some examples the flow resistor 33 may be provided by the material as discussed above that provides a structure for holding or providing the flavouring within the flavouring reservoir. In such examples this material thus provides dual functionality of flavour carrying and flow restriction.

Thus there have now been described examples of implementing the operation and structure of an aerosol delivery device that utilises secondary heat from an aerosol generation structure to warm a flavouring source to facilitate distribution of flavouring from the flavouring source to incoming air before that incoming air reaches the aerosol generation structure.

Figure 10:
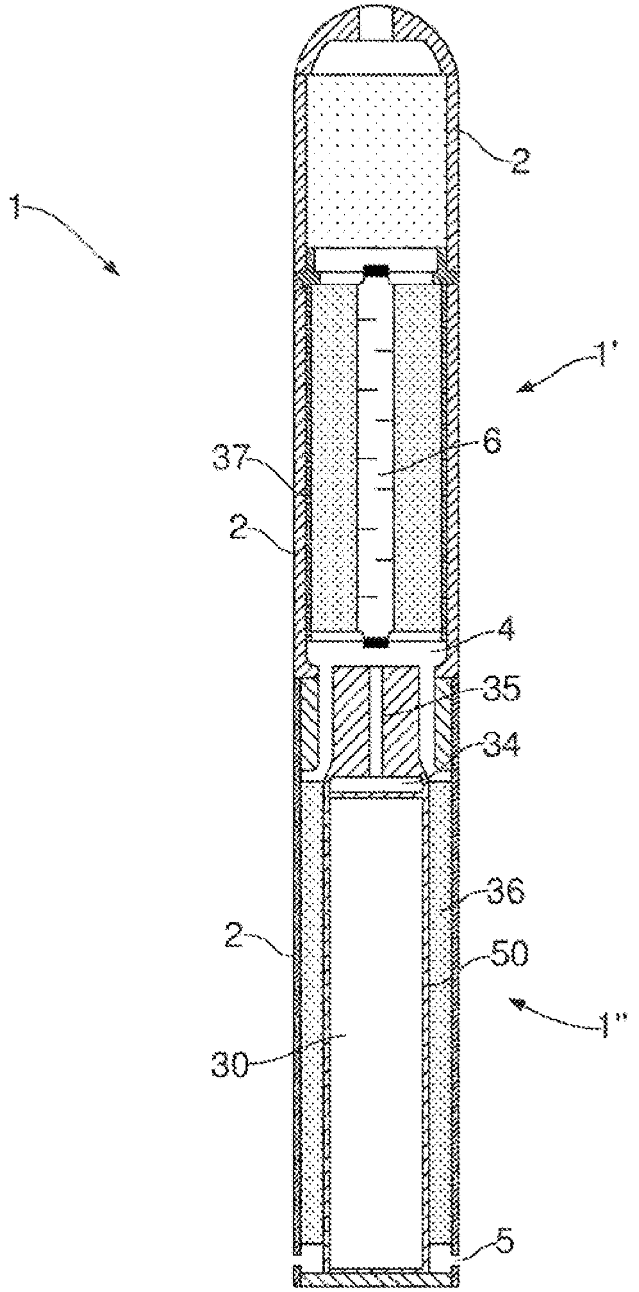
FIG. 10 shows cross-sectional side view of an aerosol delivery device comprising an aerosol-forming member according to another example.

FIG. 10 illustrates another example of an aerosol delivery device. The aerosol delivery device 1 comprises an aerosol delivery portion 1' and a power portion 1". In the present example, the aerosol delivery portion 1' and power portion 1" are arranged as separate regions of a single, unitary, aerosol delivery device 1 having a single housing 2 that houses both portions. In other examples, the aerosol delivery portion 1' and power portion 1" can be removably connected to enable a given power portion 1" to receive a number of different aerosol delivery portions 1' and/or to enable a given aerosol delivery portion 1' to receive a number of different power portions 1". In such alternative examples, the housing 2 may be openable to enable replacement of one portion or component (such as a power source 30) or may be divided in correspondence to the division of the portions such that each portion includes its own respective housing part.

The aerosol delivery device 1 may be configured to be re-usable or disposable. In the example in which the aerosol delivery portion 1' and power portion 1" are separable or openable, either or both of the aerosol delivery portion 1' and power portion 1" may be configured as being re-usable or disposable.

In this example, the portably power source 30 (which may be a battery or other portably power source as discussed with reference to FIG. 1 above) does not use the full diameter of the housing 2, but rather has located thereabout (either wholly surrounding or adjacent in part) the gas pathway from the inlet 5 to the plenum chamber 4. As in the previous examples, this gas pathway has arranged therein a flavouring reservoir 36. The flavouring reservoir 36 operates in the same manner as that discussed with reference to FIGS. 1 and 2 above, save in the arrangements for warming of the flavouring reservoir 36.

As in the example described above, as fresh air moves through the inlet passage it passes over or through the flavouring reservoir 36 which results in the release of flavours. The flavours disperse in the air and are taken downstream together with the air. The flavour enriched/flavoured air is then collected in the plenum chamber 4. The plenum chamber 4 acts to provide uniformity to the flow of air to the aerosol chamber 6/tubular channel 18. In the configuration of the present example, the air inside the inlet passage and the aerosol inside the tubular channel 18 (aerosol chamber 6) are flowing in like directions but are separated by axial offset between the centre of flow through the inlet passage and tubular channel and by the plenum chamber 4.

In the example of FIG. 10, two options for transfer of heat to the flavouring reservoir 36 can be employed, either independently or in combination.

In the first of these options, the property of many batteries to experience a slight temperature increase when supplying current is utilised. Thus, when the portable power supply 30 is a battery or other power supply that tends to experience a temperature increase when supplying current, the heat generated by the power supply 30 may be used to provide the supply of heat to the flavouring reservoir 36 arranges about or adjacent the power supply 30.

The second of these options utilises a separate heat generation that provides heat for the flavouring reservoir 36 other than by way of conducting secondary heat from the aerosol forming member 10. Such separate heat generation could be provided by providing for the control circuit 34 to allow a low of current through one or more conductive structures in or adjacent to the flavouring reservoir 36 at the same time as the provision of current to the aerosol forming member 10.

As in the example described above, this conductive heat transfer enables the flavouring reservoir 36 to reach temperatures that it would not reach otherwise, enabling enhanced release of flavours inside the reservoir.

Thus there have now been described examples of implementing the operation and structure of an aerosol delivery device that utilises secondary heat from an aerosol generation structure or an alternative heat source to warm a flavouring source to facilitate distribution of flavouring from the flavouring source to incoming air before that incoming air reaches the aerosol generation structure. It will be seen that the examples presented provide a compact structure.

It will be appreciated that implementations may also be provided in which no addition heat provision is made to the flavouring source and instead the incoming air is passed through the flavouring reservoir without heating of the flavouring reservoir before the air reaches the aerosol generation structure.

The above described embodiments of the aerosol-forming member 10 of the aerosol delivery device 1 are described for use with a solution. It should be understood that this solution may comprise certain constituents or substances that may have a stimulatory effect on the user. These constituents or substances may be of any kind that is suitable for being delivered via inhalation. The solution in which the constituents or substances are held or dissolved may primarily consist of water, ethanol, glycerol, propylene glycol or mixtures of the aforementioned solvents. By means of a sufficiently high degree of dilution in an easily volatile solvent, such as ethanol and/or water, even substances which are otherwise difficult to evaporate can evaporate in a substantially residue-free manner, and thermal decomposition of the liquid material can be avoided or significantly reduced.

It should be understood that the term "channel" used herein is not limited to a specific cross-section. Furthermore, the channel may be completely enclosed about the longitudinal axis of the channel, however it should also be appreciated that the channel may not be enclosed but open along a section parallel to the longitudinal axis of the channel.

It is also envisaged that the aerosol-forming member 10 according to any of the embodiments described above may be oxidised or coated with a non-conductive material so as to prevent a short circuit.

This disclosure shows by way of illustration various embodiments in which the present teachings may be practiced and provide for an aerosol-forming member, aerosol delivery device component and aerosol delivery device. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist in essence of, various combinations of the disclosed elements, components, features, parts, steps, means, etc. In addition, the disclosure includes other teachings not presently claimed, but which may be claimed in future.

The invention claimed is:

1. An aerosol delivery device comprising:

an air inlet;

an aerosol chamber arranged to provide an aerosol in air passing therethrough; and an aerosol outlet;

the air inlet, the aerosol chamber, and the aerosol outlet are arranged in fluid communication in that order;

wherein the aerosol delivery device further comprises a refining member containing flavoring agents for releasing into the aerosol; and wherein the air inlet surrounds the aerosol chamber.

2. The aerosol delivery device of claim 1, wherein the aerosol delivery device further comprises a housing, wherein the refining member is provided in the housing.

3. The aerosol delivery device of claim 1, further comprising a mouthpiece, wherein the mouthpiece at least partially covers the refining member.

4. The aerosol delivery device of claim 3, wherein the refining member is engageable with the mouthpiece.

5. The aerosol delivery device of claim 3, wherein the refining member is configured to engage with an outer wall of the mouthpiece.

6. The aerosol delivery device of claim 3, wherein the aerosol outlet is in fluid communication with a mouthpiece outlet arranged to deliver the aerosol therethrough when suction is applied to the mouthpiece.

7. The aerosol delivery device of claim 1, further comprising an aerosol forming member arranged to generate the aerosol in air passing through the aerosol chamber.

8. The aerosol delivery device of claim 7, wherein the aerosol forming member comprises a heating element arranged to generate a condensation aerosol.

9. The aerosol delivery device of claim 8, further comprising a liquid reservoir in fluid communication with the heating element and arranged to deliver liquid to the heating element, the heating element arranged to generate the aerosol by evaporation of liquid therefrom.

10. The aerosol delivery device of claim 7, further comprising a switch to provide activation of the aerosol forming member responsive to a flow of air from the inlet toward the outlet.

11. The aerosol delivery device of claim 1, further comprising a flow resistor downstream of the air inlet and upstream of the aerosol chamber.

12. An aerosol delivery portion for use with an aerosol delivery device comprising: the aerosol delivery portion and a power portion which is configured to be removably connected to the aerosol delivery portion, wherein the aerosol delivery portion comprises:

an air inlet;

an aerosol chamber arranged to provide an aerosol in air passing therethrough; and an aerosol outlet;

the air inlet, the aerosol chamber, and the aerosol outlet are arranged in fluid communication in that order;

wherein the air inlet surrounds the aerosol chamber; and wherein the aerosol delivery device further comprises a refining member containing flavoring agents for releasing into the aerosol.

13. A device configured to impart flavoring agents, from a refining member of the device, to an airstream admitted to the device after the airstream reaches an aerosol generator of the device, the device thereby operable to deliver the flavoring agents from the refining member into an aerosol, wherein the airstream is admitted to the device from an air inlet of the device, and wherein the air inlet surrounds the aerosol generator.

14. The device of claim 13, further comprising a power source to heat the aerosol generator for the generation of the aerosol in the airstream.

15. The device of claim 13, wherein the device further comprises a housing, wherein the refining member is provided in the housing.

16. The device of claim 13, further comprising a mouthpiece, wherein the mouthpiece at least partially covers the refining member.

17. A method of generating a flavored aerosol in an aerosol delivery device, wherein the aerosol delivery device comprises an aerosol generator and an air inlet which surrounds the aerosol generator, the method comprising:

generating an aerosol by passing an airflow, which originates from the air inlet, through the aerosol generator that evaporates a liquid into the airflow to create the aerosol; and delivering the aerosol to a mouthpiece of the aerosol delivery device, wherein the method further comprises:

releasing flavoring agents from a refining member, from the aerosol delivery device, into the aerosol.

18. The method of claim 17, wherein the refining member is provided in a housing of the aerosol delivery device.

19. The method of claim 17, wherein the mouthpiece at least partially covers the refining member.

20. An aerosol delivery device comprising:

an air inlet;

an aerosol chamber arranged to provide an aerosol in air passing therethrough;

a housing;

a mouthpiece comprising an aerosol outlet configured to receive a generated aerosol from the aerosol delivery device; and a refining member containing flavoring agents for releasing into the aerosol;

wherein the air inlet surrounds the aerosol chamber; and wherein the mouthpiece at least partially engages the refining member.

* * * * *